United States Patent
Krinke

(10) Patent No.: US 9,492,650 B2
(45) Date of Patent: Nov. 15, 2016

(54) IONTOPHORETIC DRUG DELIVERY PACKAGING

(75) Inventor: Todd A. Krinke, Buffalo, MN (US)

(73) Assignee: TEVA PHARMACEUTICALS INTERNATIONAL GMBH, Rapperswil-Jona (CH)

( * ) Notice: Subject to any disclaimer, the term of this patent is extended or adjusted under 35 U.S.C. 154(b) by 321 days.

(21) Appl. No.: 12/597,950

(22) PCT Filed: Sep. 3, 2009

(86) PCT No.: PCT/US2009/004969
§ 371 (c)(1),
(2), (4) Date: Oct. 28, 2009

(87) PCT Pub. No.: WO2010/027468
PCT Pub. Date: Mar. 11, 2010

(65) Prior Publication Data
US 2012/0022431 A1    Jan. 26, 2012

Related U.S. Application Data

(60) Provisional application No. 61/094,442, filed on Sep. 5, 2008.

(51) Int. Cl.
*A61N 1/04* (2006.01)
*A61N 1/30* (2006.01)
*A61N 1/32* (2006.01)

(52) U.S. Cl.
CPC ........... *A61N 1/0448* (2013.01); *A61N 1/0428* (2013.01); *A61N 1/044* (2013.01); *A61N 1/30* (2013.01); *A61N 1/303* (2013.01); *A61N 1/325* (2013.01)

(58) Field of Classification Search
CPC ................. A61N 1/30; A61N 1/303; A61N 1/0436; A61N 1/044; A61N 1/0448; A61N 1/325; A61N 1/0428
(Continued)

(56) References Cited

U.S. PATENT DOCUMENTS 4,666,441 A  *  5/1987  Andriola et al. ............. 424/448
4,695,464 A      9/1987  Alderman
(Continued)

FOREIGN PATENT DOCUMENTS

| CN | 1780661 | 5/2006 |
|---|---|---|
| JP | 2006513768 | 9/2004 |
| JP | 2007504110 A | 7/2007 |

OTHER PUBLICATIONS

"Adjacent." Merriam-Webster. Merriam-Webster. Web. Oct. 15, 2014. <http://www.merriam-webster.com/dictionary/adjacent>.*
(Continued)

*Primary Examiner* — Imani Hayman
*Assistant Examiner* — Nilay Shah
(74) *Attorney, Agent, or Firm* — Baker & Hostetler LLP

(57) ABSTRACT

The present invention relates generally to iontophoretic drug delivery systems for transdermal delivery of therapeutic agents and, more particularly, to packaging such systems for long shelf life and easy assembly for use. The system package includes an iontophoretic skin worn patch component that accommodates a power source, electronics, electrodes and a drug pack component that carries a therapeutic agent which is contained as a separate sealed component. The packaged system further provides for ease of assembly at the time of use.

25 Claims, 17 Drawing Sheets

(58) Field of Classification Search
USPC ........ 604/20, 501; 156/69; 53/396; 206/363; 128/897
See application file for complete search history.

(56) References Cited

U.S. PATENT DOCUMENTS

| | | | |
|---|---|---|---|
| 4,911,707 A * | 3/1990 | Heiber et al. | 424/449 |
| 5,128,137 A * | 7/1992 | Muller et al. | 424/449 |
| 5,320,598 A * | 6/1994 | Haak et al. | 604/20 |
| 5,730,716 A | 3/1998 | Beck et al. | |
| 5,738,647 A * | 4/1998 | Bernhard et al. | 604/20 |
| 5,817,044 A * | 10/1998 | Evers et al. | 604/20 |
| 6,223,075 B1 * | 4/2001 | Beck et al. | 604/20 |
| 6,587,717 B1 * | 7/2003 | Kuribayashi et al. | 604/20 |
| 6,615,078 B1 * | 9/2003 | Burson et al. | 604/20 |
| 6,654,635 B1 * | 11/2003 | Koga et al. | 604/20 |
| 6,745,071 B1 * | 6/2004 | Grace et al. | 604/20 |
| 2003/0060797 A1 * | 3/2003 | Fischer | 604/501 |
| 2004/0166147 A1 | 8/2004 | Lundy et al. | |
| 2005/0193554 A1 * | 9/2005 | Young et al. | 29/825 |
| 2005/0228336 A1 * | 10/2005 | Keusch et al. | 604/20 |
| 2011/0152743 A1 * | 6/2011 | Adachi et al. | 604/20 |

OTHER PUBLICATIONS

International Search Report dated Nov. 13, 2009, for International Application No. PCT/US09/04969, filed Sep. 3, 2009.
Written Opinion of the International Searching Authority dated Nov. 2, 2009, for International Application No. PCT/US09/04969, filed Sep. 3, 2009.
Notification Concerning Transmittal of International Preliminary Report on Patentability (Chapter 1 of the Patent Cooperation Treaty) with International Preliminary Report on Patentability dated Mar. 17, 2011 from the International Bureau of WIPO, 11 pages.
Translation of Office Action for JP Patent Application 2011-526043, mailed Jun. 28, 2013, 5 pages.

* cited by examiner

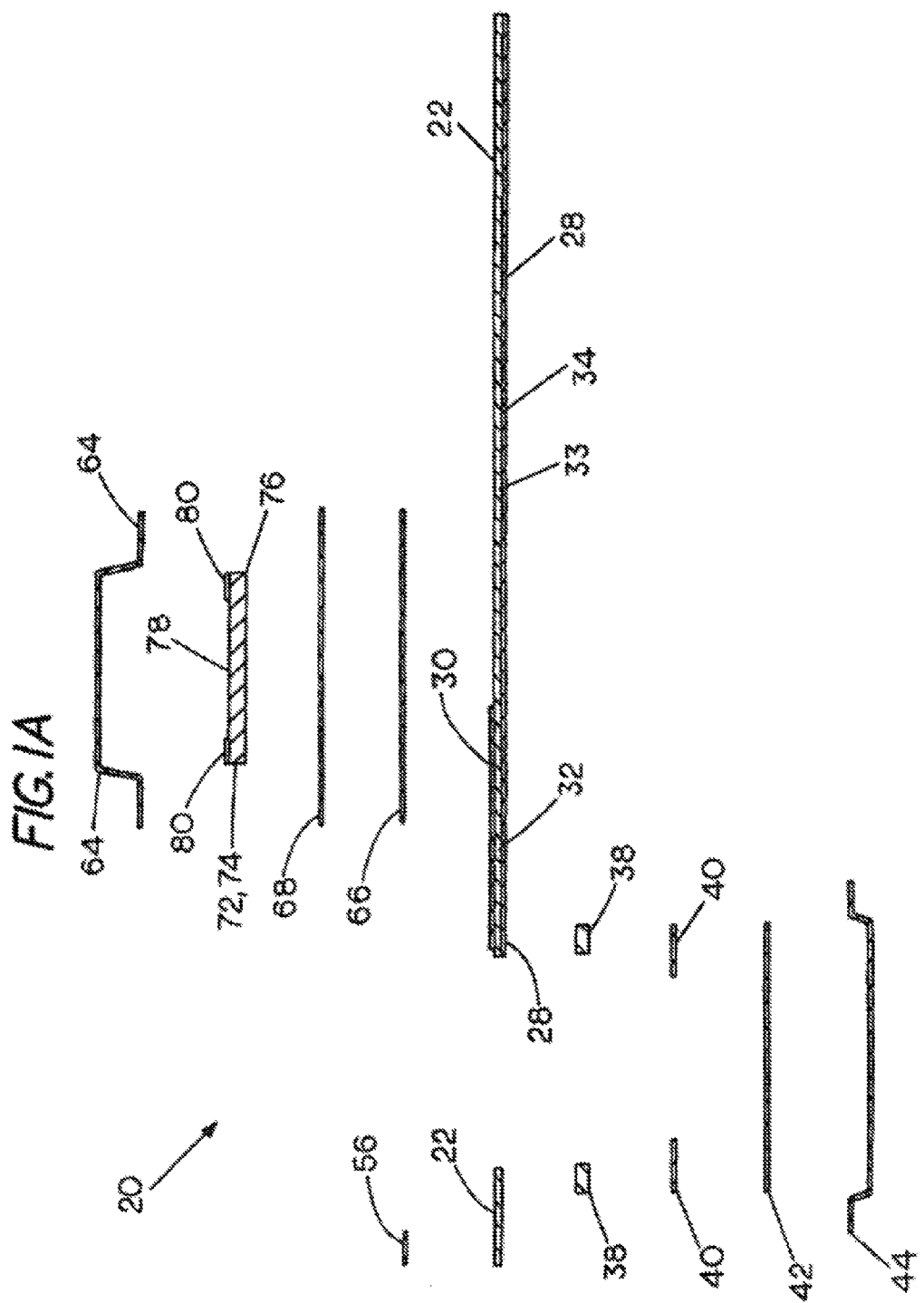

Cross Section of a Portion of the Printable Card Stock

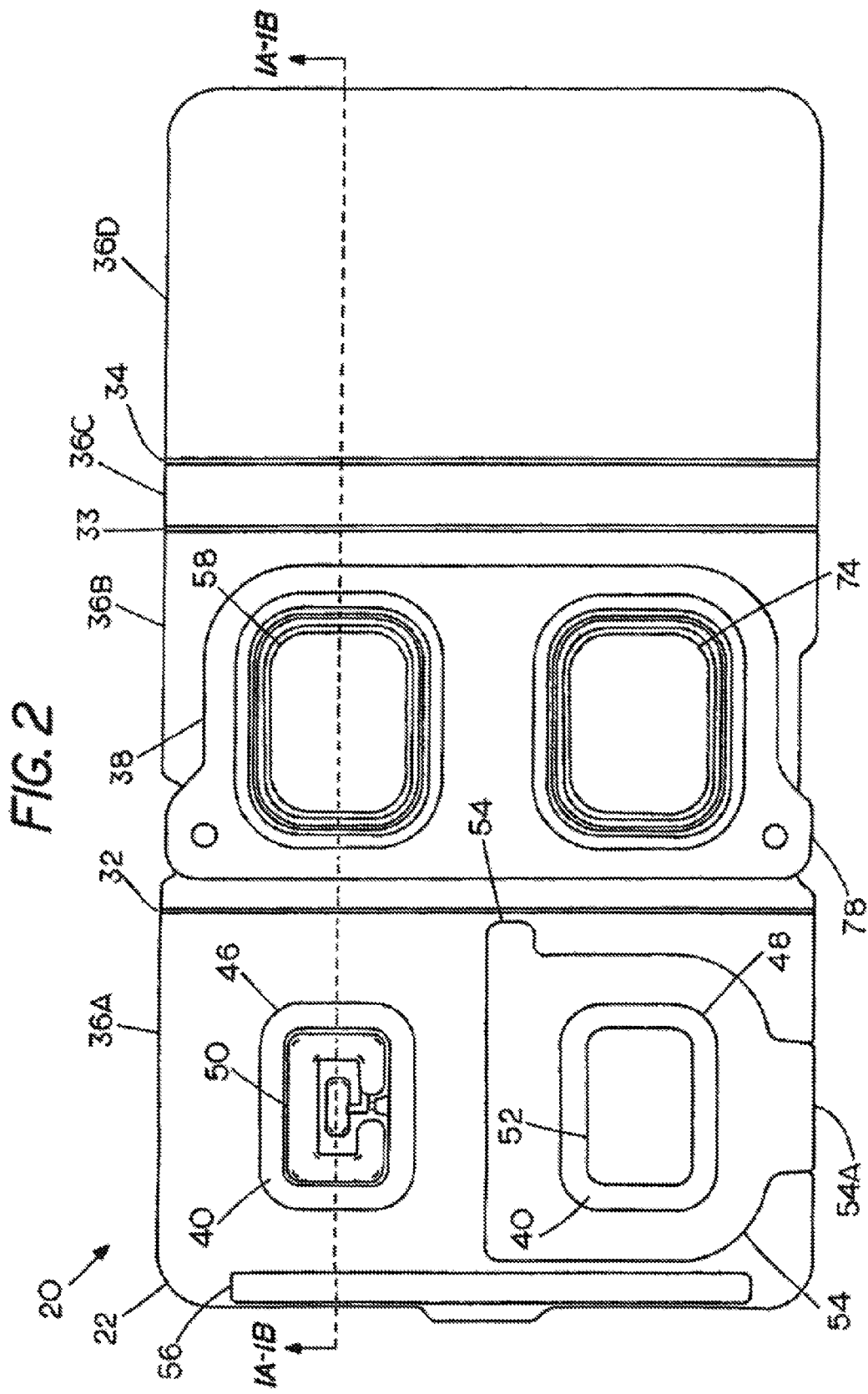

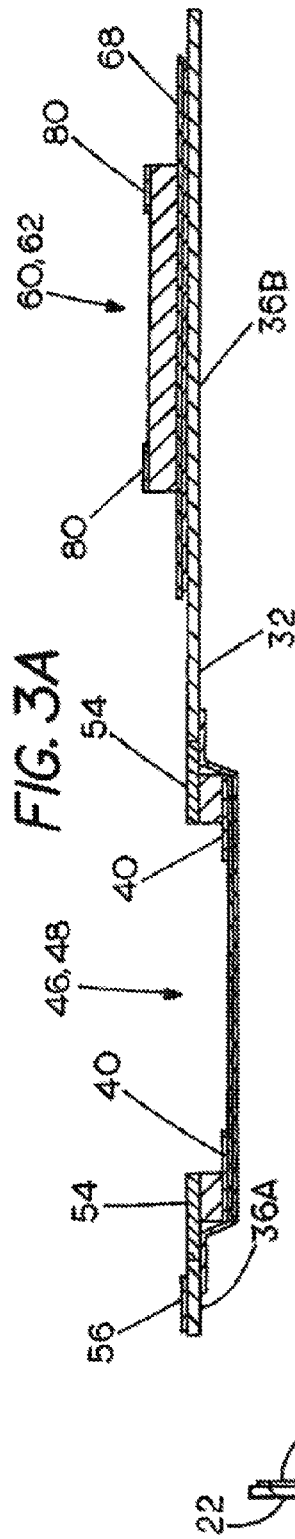
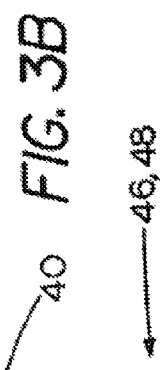
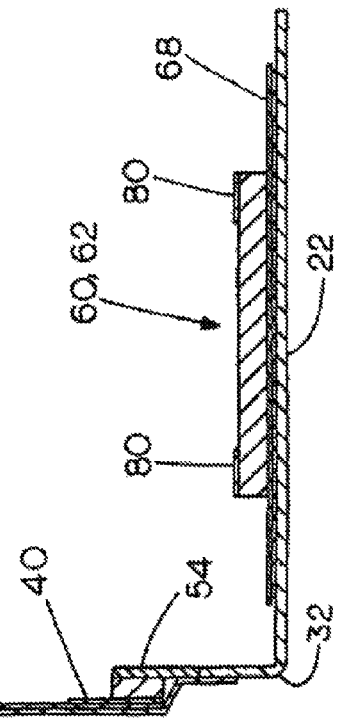
FIG. 3A
FIG. 3B

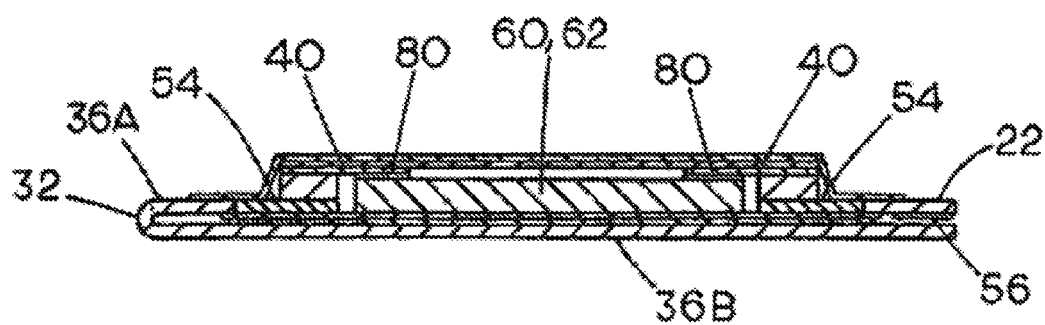
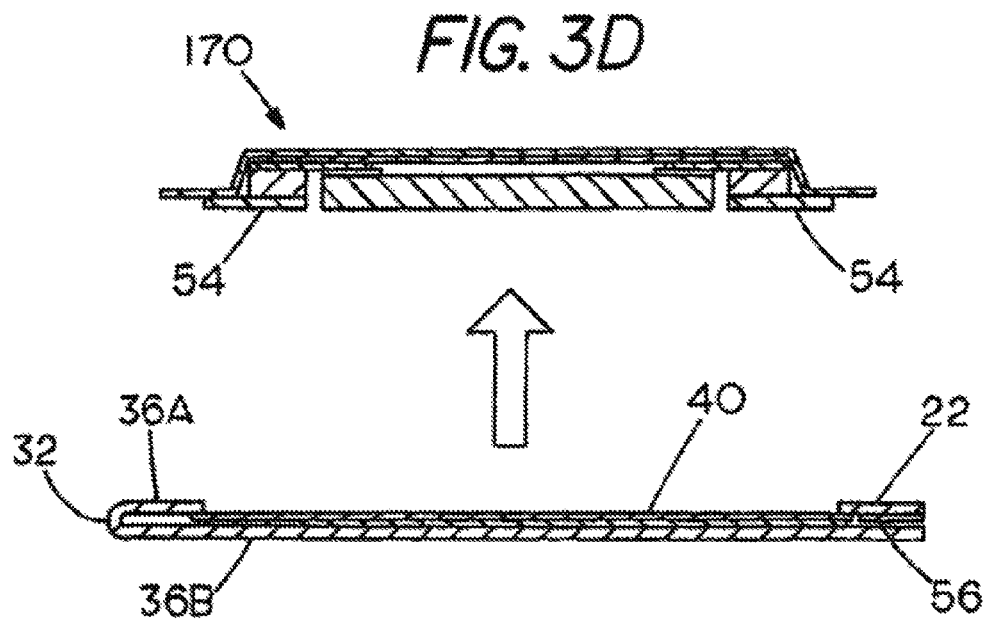

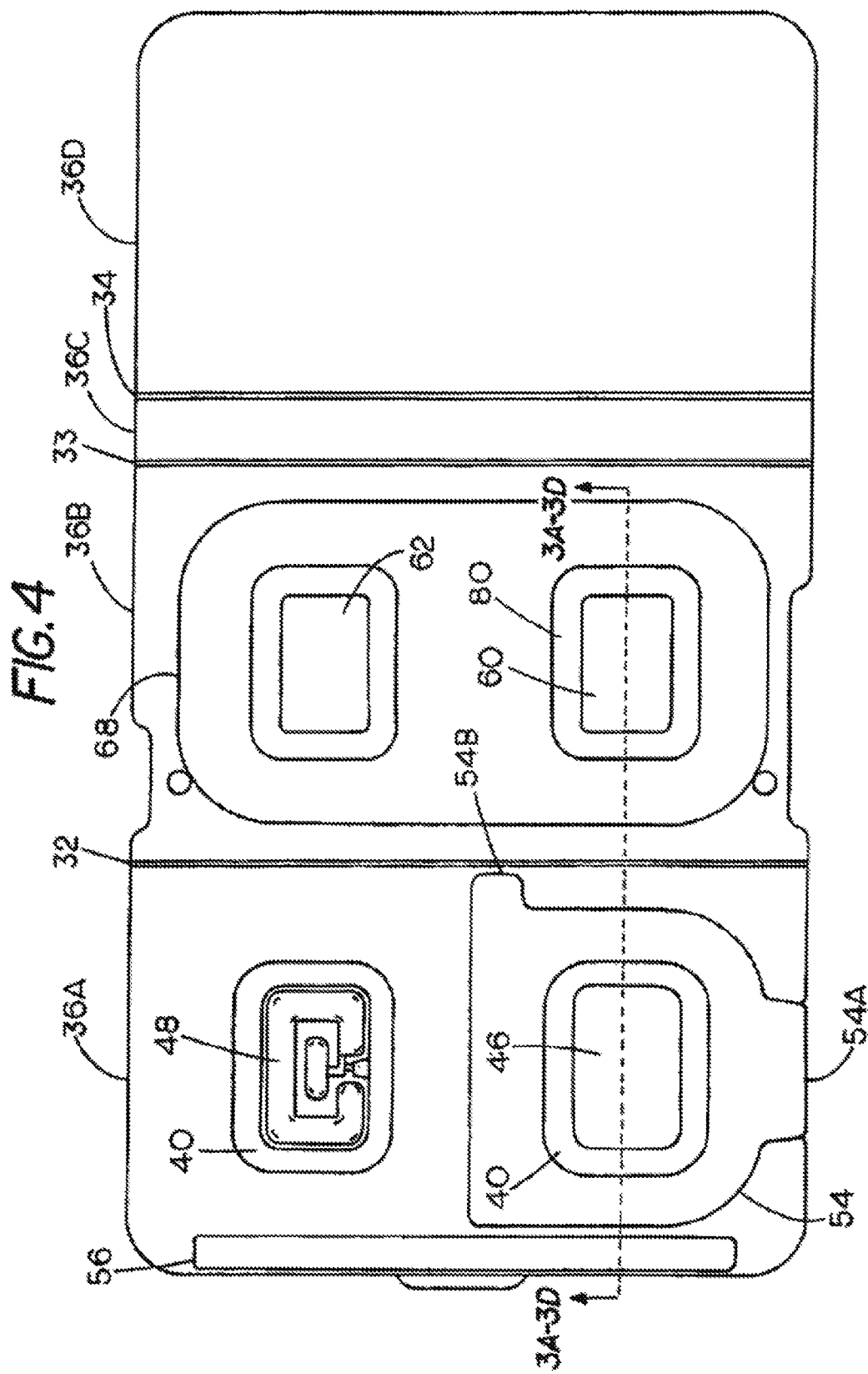

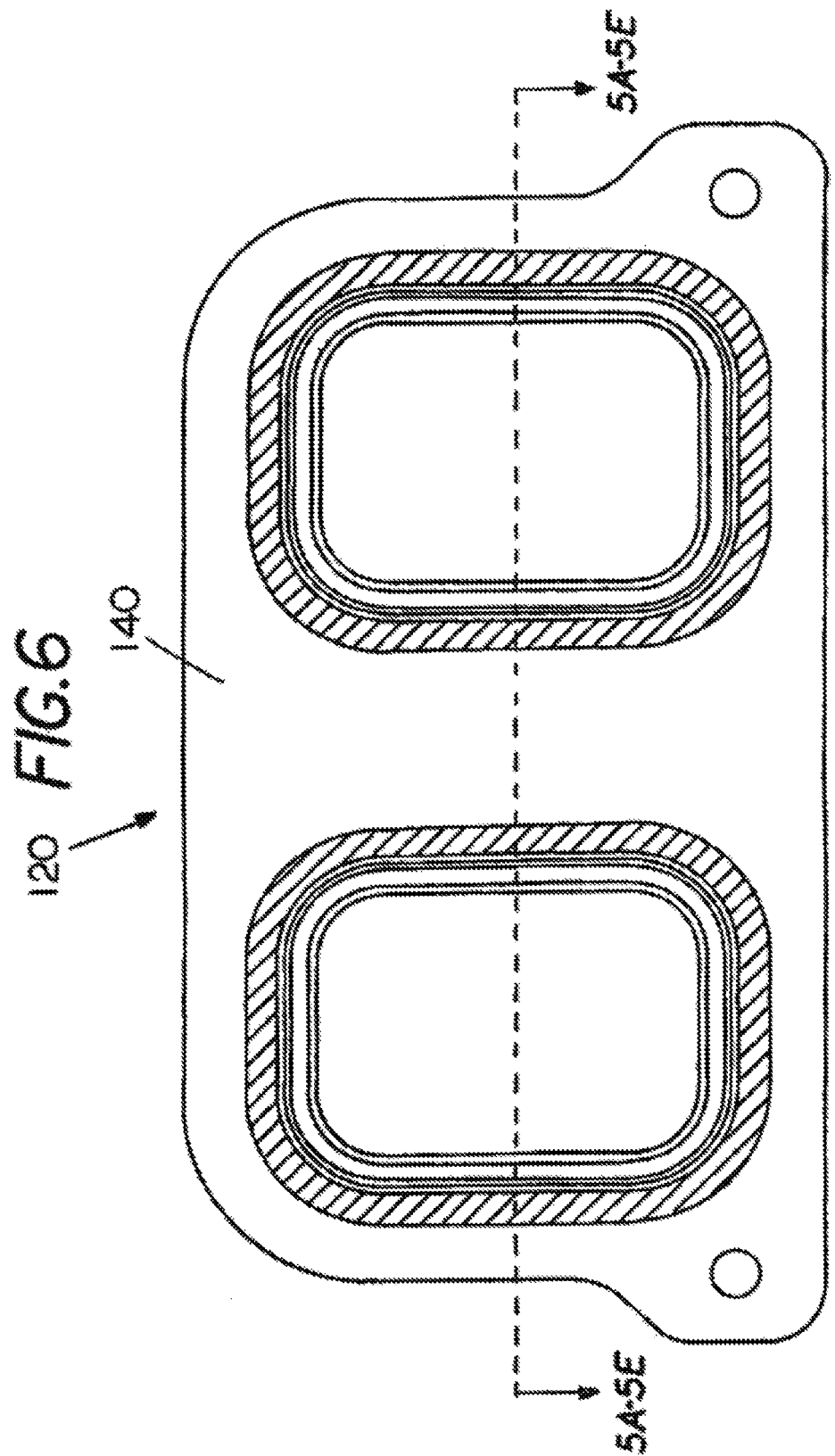

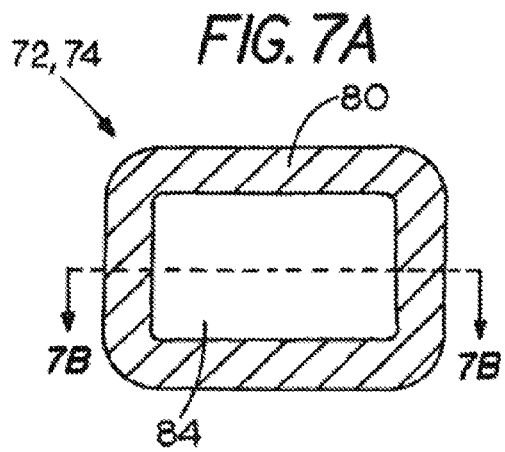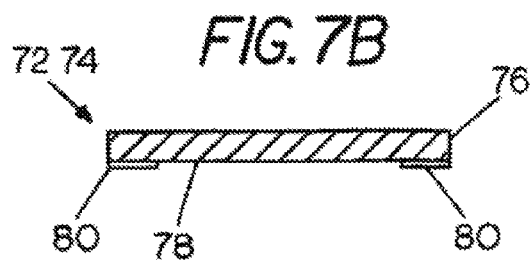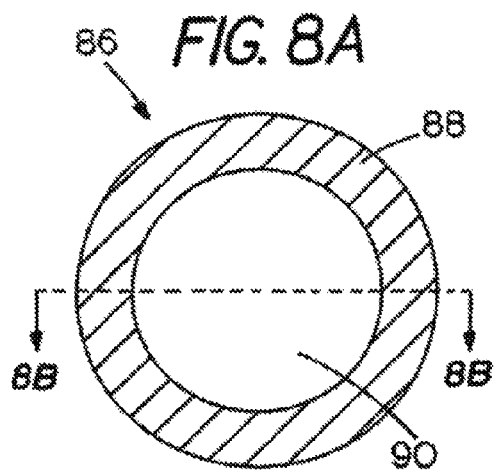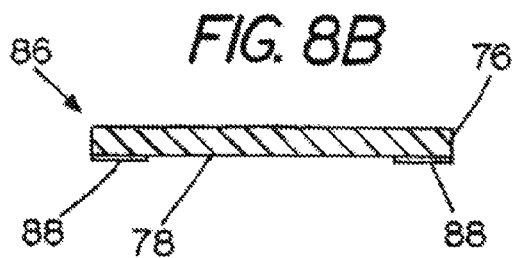

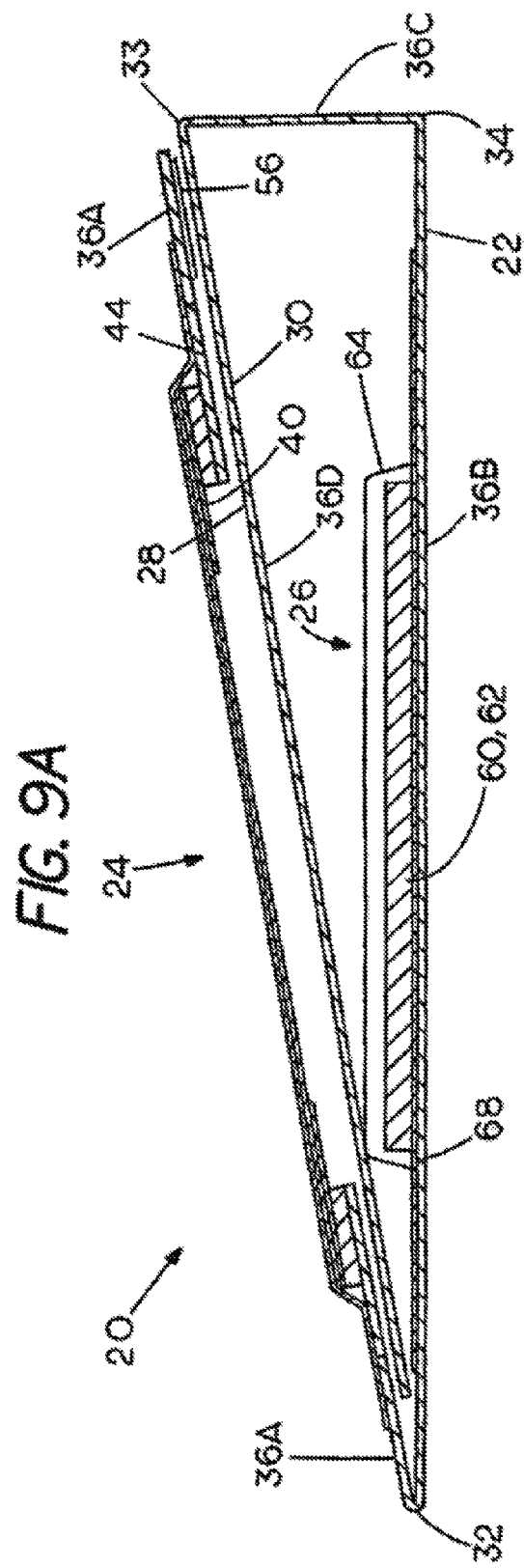

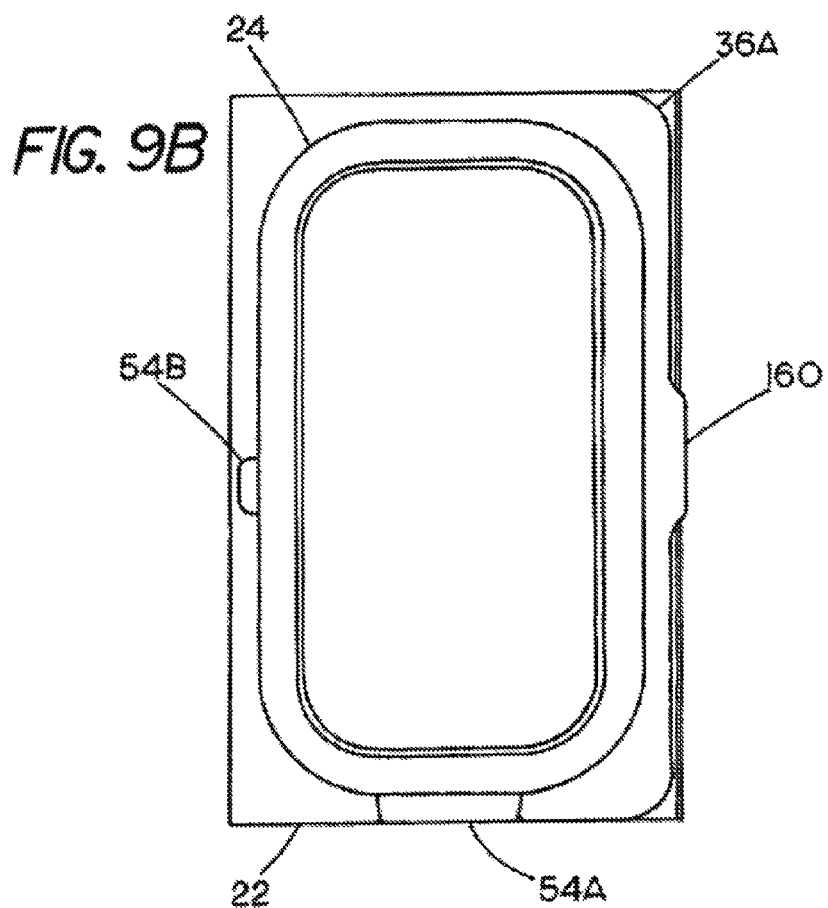
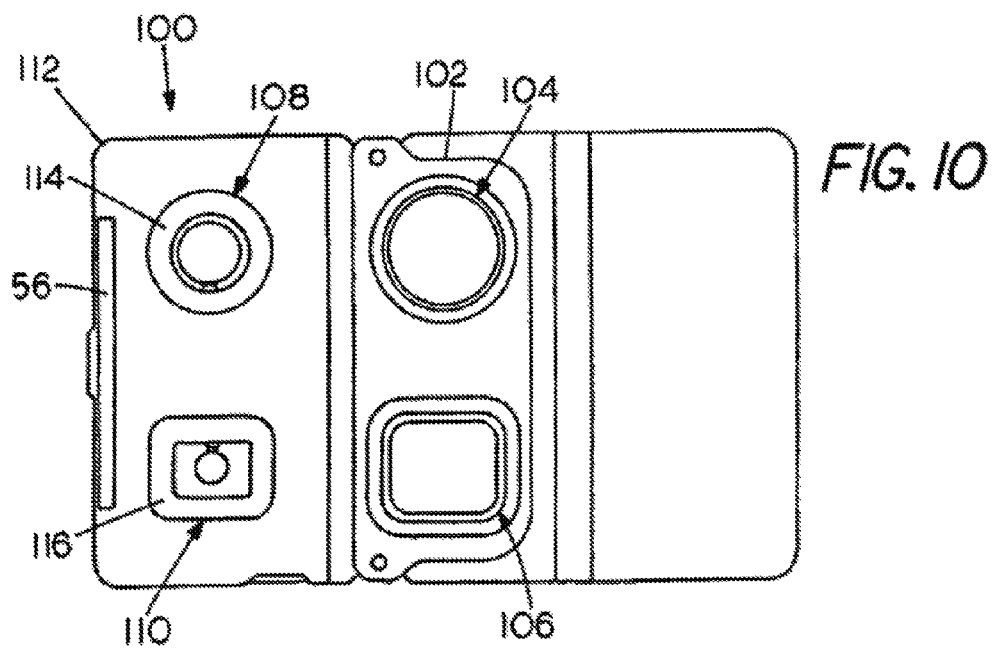

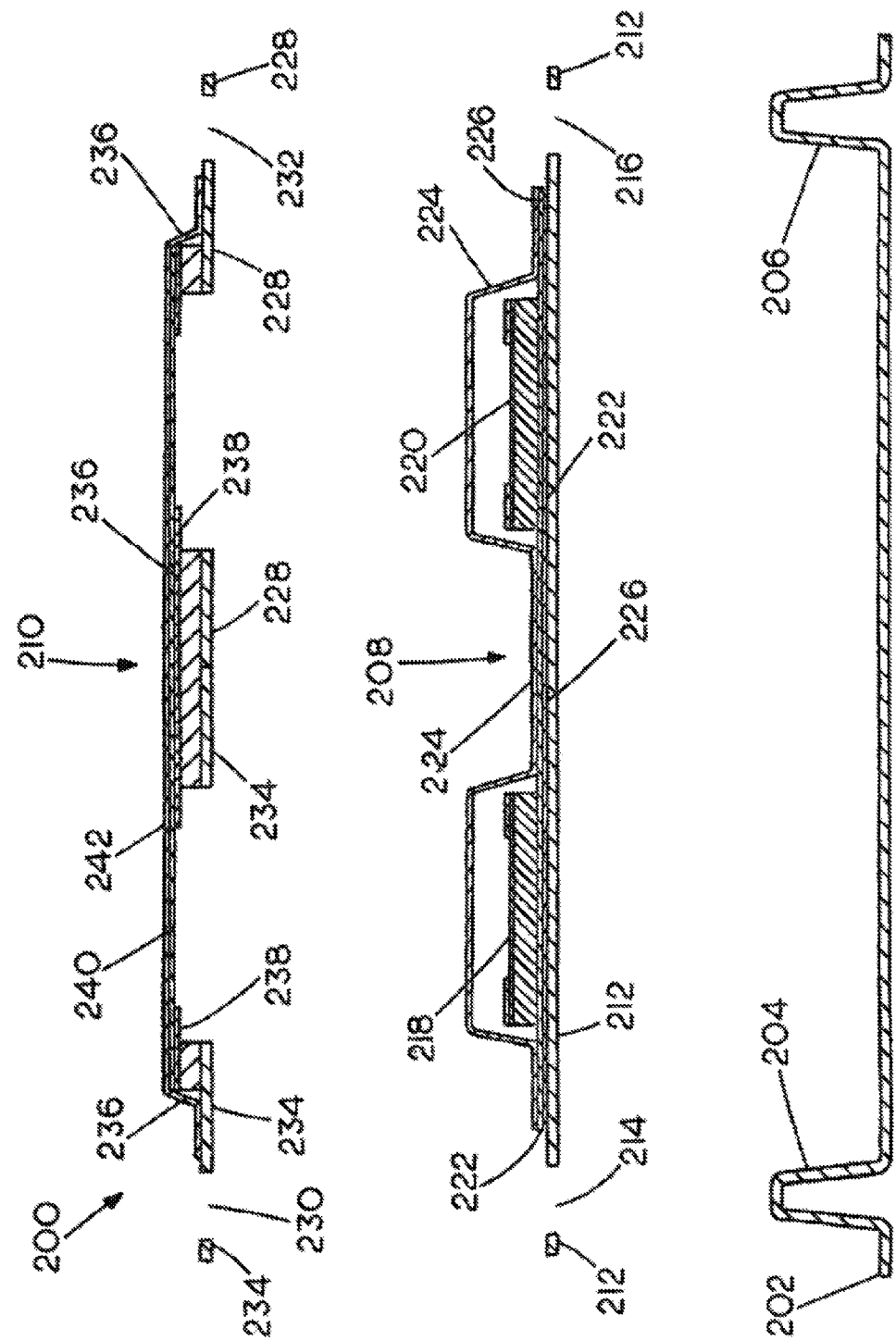

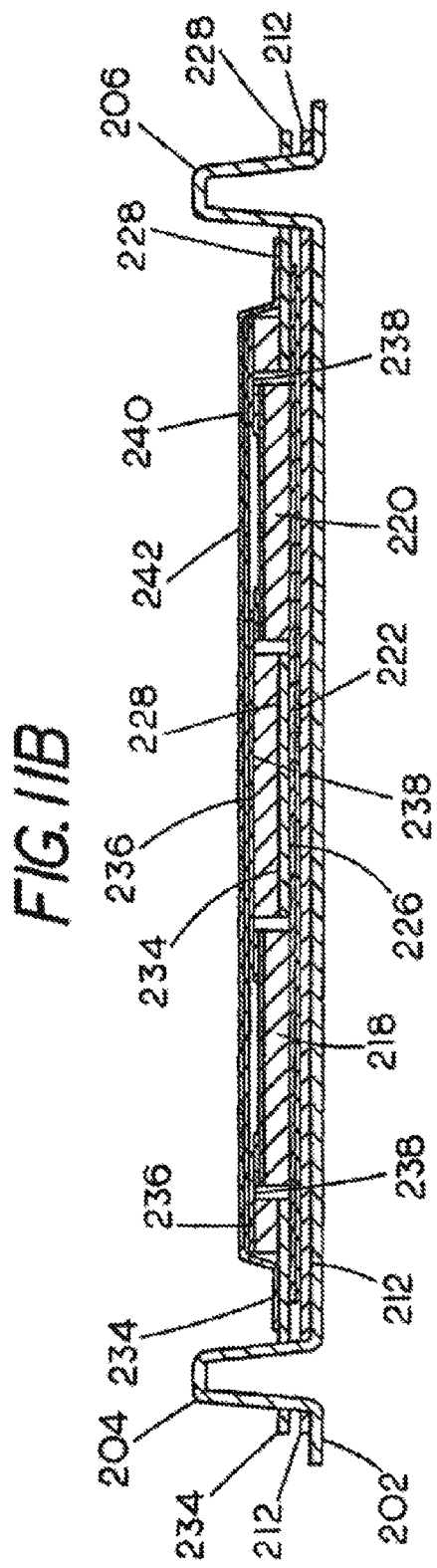

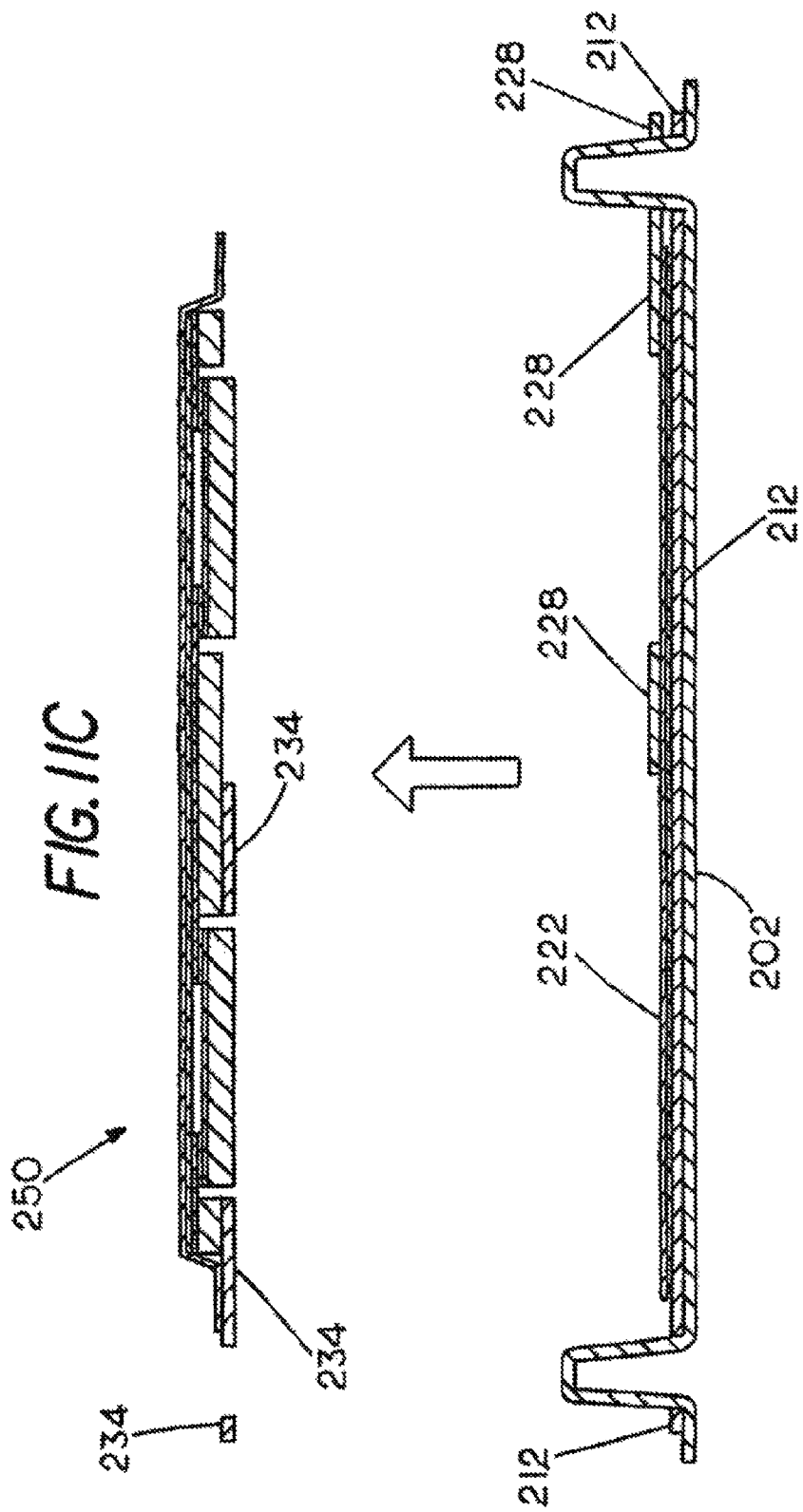

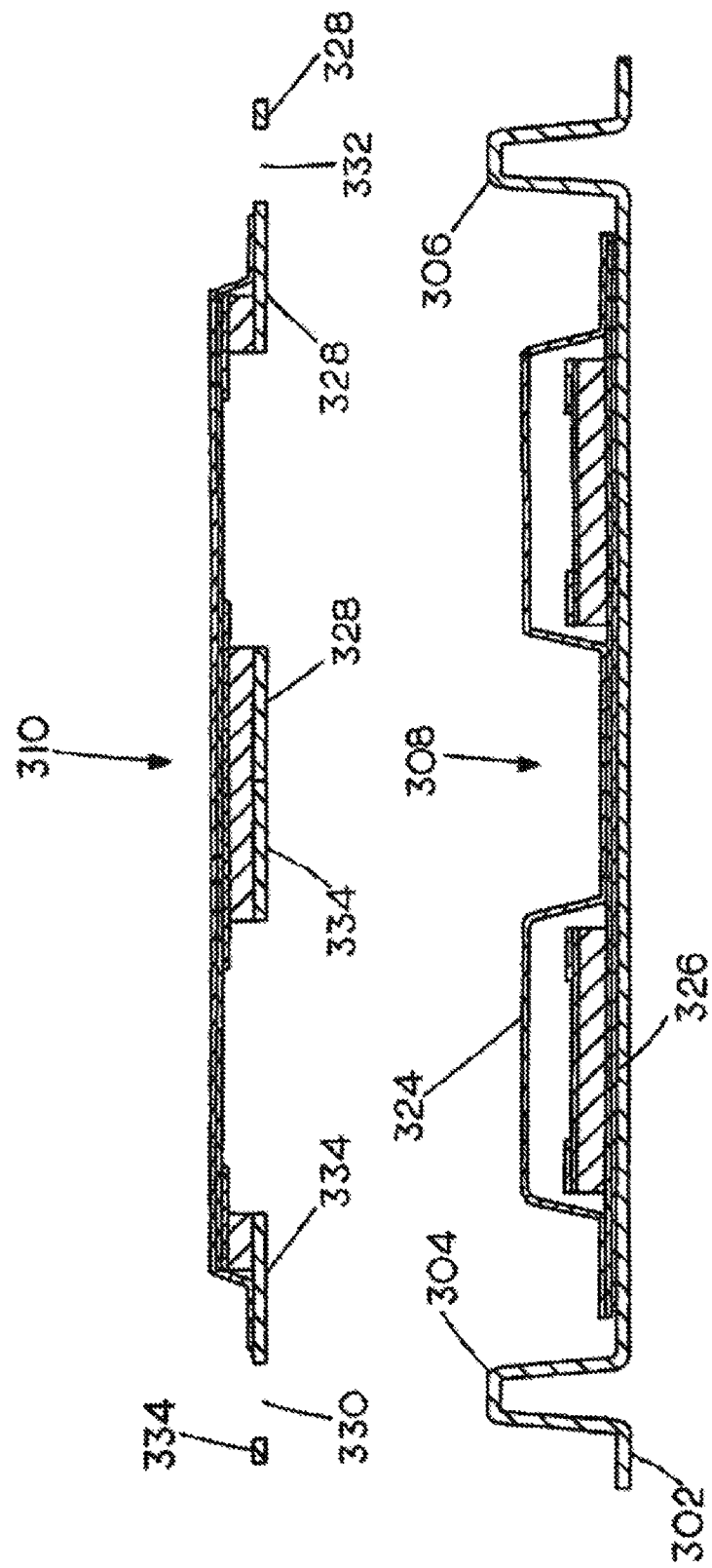

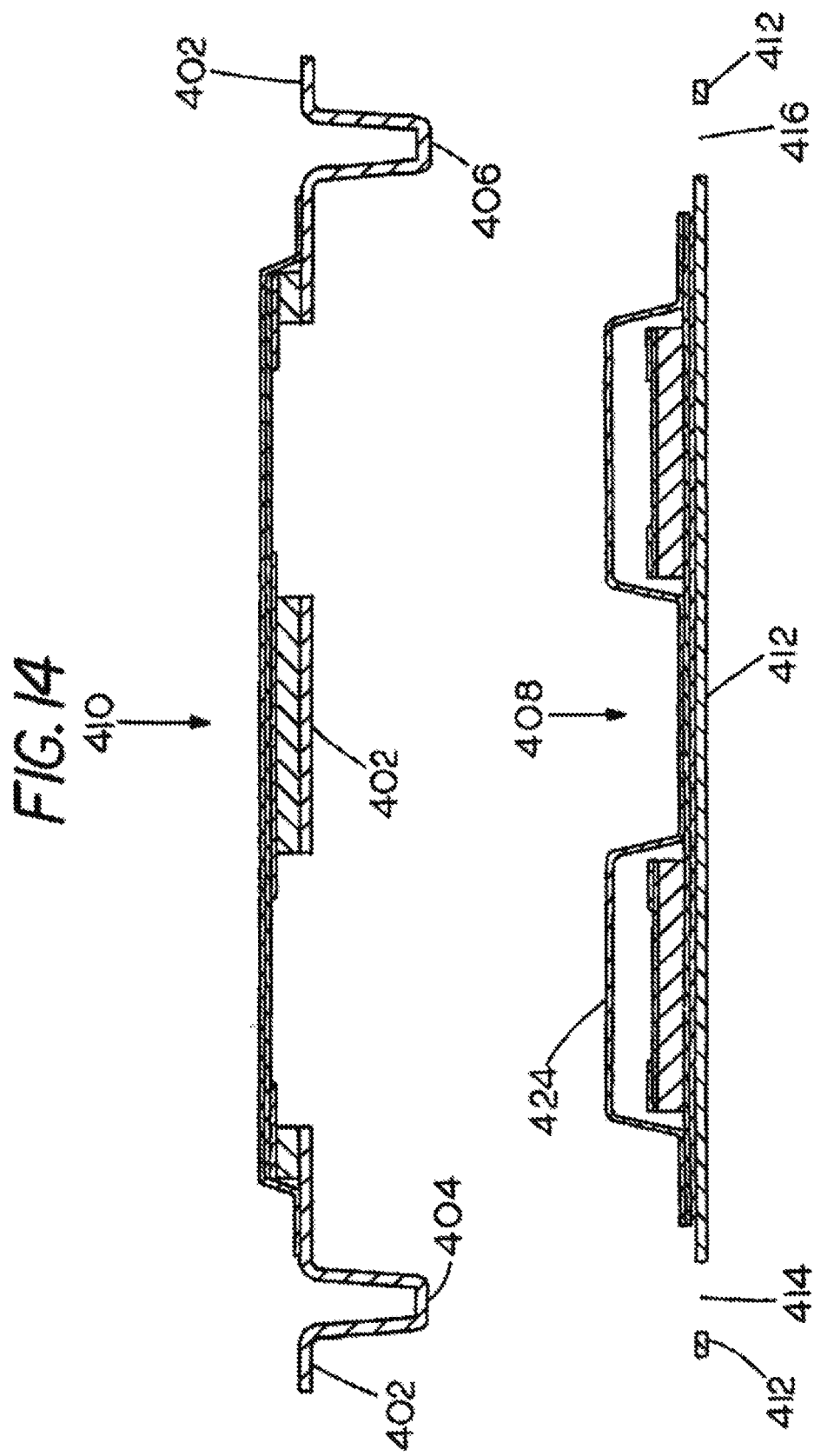

IONTOPHORETIC DRUG DELIVERY PACKAGING

CROSS-REFERENCED TO RELATED APPLICATIONS

This application is a non-provisional application of Application No. 61/094,442, filed Sep. 5, 2008 and claims priority from that application which is also deemed incorporated by reference in its entirety in this application.

BACKGROUND OF THE INVENTION

I. Field of the Invention

The present invention relates generally to iontophoretic drug delivery systems for transdermal delivery of therapeutic agents and, more particularly, to packaging such systems for long shelf life and easy assembly for use. The system package includes an iontophoretic skin worn patch component that accommodates a power source, electronics, electrodes and a drug pack component that carries a therapeutic agent which is contained as a separate sealed component. The packaged system further provides for ease of assembly at the time of use.

II. Introduction

The process of iontophoresis is well known and has found significant commercial use in the delivery of ionically charged compounds across the skin at the sites of system electrodes of like charge.

Self-contained, wearable iontophoretic systems have been developed in which the electrical circuitry and power supply have been integrated into a single, skin-worn patch. In many of these devices, drug ions are delivered into the body from an aqueous 'drug' reservoir contained in the iontophoretic device, and counter ions of opposite charge are delivered from a 'counter' reservoir. Because drug/ion solutions are often stored remotely in bulk quantity and introduced to an absorbent layer of the iontophoresis electrode of interest at the time of use, additional steps are necessary to incorporate drug ions and counter ions into the device. However, the electrodes can be easily over-filled or under-filled, thus this aspect requires trained personnel with good technique. Additionally, because the drug solution is stored separately from the electrodes, management of two inventories is required.

To avoid the need for users to incorporate the aqueous drug or ion reservoir at the time of use, the drug solution can be pre-packaged with an electrode, or an aqueous reservoir can be stored in contact with an electrode assembly, and a dry medicament layer introduced to the aqueous reservoir at the time of use. Unfortunately, with either configuration, an electrode is still stored in wet environment, and that and other components may succumb to corrosive deterioration.

For the above and other reasons, co-packaging iontophoretic transdermal drug delivery patches with active pharmaceuticals remains a challenging problem. Because iontophoretic patches contain electrodes and electronics and the drug solution is usually aqueous in nature, without a barrier between the aqueous environment and the electronics, degradation of both the electronics and the drug solution will occur within the desired shelf life, which may be 2 years. A packaging solution that provides a barrier and therefore meets shelf life requirements between the electronics and the drug solution, yet still allows the drug solution and electrodes to be combined in an assembled device at time of use is sought. A solution that not only addresses shelf life stability issues surrounding co-packaging aqueous drug solutions with electrodes and electronic circuits but which also makes it easier for the operator or user to activate and apply the patch is even more desirable.

SUMMARY OF THE INVENTION

The present invention presents a pre-packaged complete iontophoretic drug delivery system that is easily assembled from the packaged state. Pre-packaged complete iontophoretic drug delivery systems of the invention include both an iontophoresis patch and an agent to be administered and enjoy a long shelf life. The system includes two main components, namely, a drug pack component containing one or more absorbent pads, at least one of which contains an active agent, and an iontophoresis patch component which contains electrodes and a source of electric power. The drug pack and patch are packaged together, but as separated components during storage of the system. They are readily incorporated into an assembled state at the time of use by the use of a built-in alignment technique that employs an alignment structure that may take any of several forms. One form includes a conjoined folding platform or support structure that carries the components on separate panels and another involves the use of a separate alignment fixture or guide element.

In one embodiment, an iontophoresis patch component and a sealed therapeutic ion-containing or an active ingredient-containing drug pack (also known as a "blister pack") component are carried in a distinct arrangement by consecutive supporting panel structures in a configuration that is designed to fold on itself in different manners to accommodate both storage and use. This type of an arrangement may be characterized as a folding configuration or folding support structure.

Alternatively, an iontophoresis patch and a sealed drug pack may be stored as separate components in a package and assembled together using an alignment fixture or guide element prior to use. The alignment fixture or guide element may be a separate component or may be packaged as initially attached to either the iontophoresis patch or the drug pack.

In addition, while most drug or therapeutic ion species generally will be contained in gel form in the drug pack, some may be carried in a dry state in the iontophoresis patch. In this arrangement, the therapeutic ion species is combined with the gel or other solution upon assembly of the system.

The folding embodiment features a plurality of consecutive conjoined panels in a platform or support structure in which a transdermal, iontophoretic patch is affixed to one panel support structure and a formed and sealed therapeutic agent chamber or drug pack is affixed to an adjacent panel with the corresponding drug and electrode parts in aligned registration and an appropriate fold line therebetween. The folding support configuration or platform preferably is fabricated with a paper board or polymer material with selectively applied release coatings and pressure sensitive tapes for affixing the transdermal patch and drug pack to the panels. The transdermal patch includes all necessary adhesive tapes, liners, electrodes, and circuit elements of a typical iontophoretic patch device except a drug imbibed absorbent pad.

The sealed drug pack is formed using low moisture vapor transmission materials and contains at least one permeable absorbent pad imbibed with the desired drug solution generally in gel form. The drug imbibed pad or pads remain separately housed in a sealed drug pack during its shelf life until time of use.

The folding configuration contains cut outs and fold lines to allow and guide various panels to fold inward or collapse on top of one another and includes a release coating (which may be siliconized) applied to the back surface with a coating on the front side having a surface on which printing can be applied. The printable coating surface may include a conventional clay material. The transdermal patch is affixed to a first panel on the release-coated or back side of the platform. The drug pack is bonded to the adjacent panel on the printable or clay coated front side. The folding system further contains cut outs in the shape and position of the adsorbent pads on the transdermal patch panel which allows the patch to communicate and register with the contents of the drug pack when the system is folded. As indicated, the patch and drug pack are registered to the panels so that when the system is folded together in an assembled arrangement, the formed blisters or drug chambers of the tray are aligned with corresponding wells of patch electrodes.

In certain of these embodiments where a folding support structure associated with said drug pack component and said iontophoresis patch component is present, the folding support structure may further include a separator component configured to physically separate the drug pack and iontophoresis patch components when the iontophoretic drug delivery system is present in a folded storage stage. As described above, in these embodiments the support structure may include a first panel that is associated with the iontophoresis patch component and a second panel that is associated with the drug pack component, where these first and second panels are joined by a fold line. The support structure further includes a separator component that is made up of one or more additional panels, e.g., joined to the second panel on a side opposite the side that the second panel is joined to the first panel, where these additional one or more panels are configured to physically separate the iontophoretic and drug pack components when the system is in the folded storage state, e.g., see FIG. 9A. The separator component not only separates the drug pack from the patch component in the folded storage state, but also acts as a protective packaging for the system components.

Storing the aqueous drug imbibed absorbent pad or pads in a generally inert sealed blister or drug pack prior to use prevents the contents from interacting with the surroundings, thereby, preventing any degradation of the drug solution or of any electronic or other patch components housed in proximity to the drug pack. In accordance with preserving the integrity of the contents, the materials in direct contact with the drug solution during storage are preferably limited to relatively inert materials. These include a formed tray, the absorbent pad and the lid or barrier layer of the blister or drug pack. Materials of low water vapor transmission include vinyls, polyesters, polyamides, including nylon, or polyalkylines, such as polyethylene and polypropylene. The material may further be coated on one or both sides with a material selected from a diverse fabric, foil, metalized film or other materials to reduce water vapor transmission still further. The tray and lid also should be formed of materials that are inert to or stable in the presence of the components of the drug solution and absorbent pads.

One embodiment includes a tray and lid of a composite aluminum/polymer material. The lid is provided with an easily peeled seal layer for easy removal at the time of use. In that embodiment, the absorbent pads consist of a lamination of suitable polymer layers and coatings that are stable in the presence of and contact with the drug solution. The absorbent pads are preferably of a non-woven matrix which has a known gel absorbency or take-up rate. Examples of materials that may be suitable for the absorbent non-woven matrix include cotton, polypropylene, polyethylene, and polyester. Preferably, the absorbent material is polypropylene.

Alternate embodiments assemble the drug delivery device system from separate components using an alignment fixture or guide element which may be furnished as a separate component or combined with a transdermal iontophoretic patch or a drug pack. Separation of the assembled wearable iontophoresis device and drug pack is similar in each case and the construction of the iontophoresis patch and drug pack is similar to that described in connection with the folding embodiments.

In the case of the folding panel embodiments, at time of use, the operator first peels off the formed drug pack tray lid held by the seal layer material exposing the drug imbibed pad or pads which remain affixed to a panel of the system. The patch component is attached to an adjacent panel. Next, the operator folds the panels together bringing the drug imbibed pads in intimate contact with the wells of the patch electrodes. The patch electrodes are provided with a ring of adhesive that bonds to a matching ring layer portion of the surface of the absorbent pads when the two are brought into contact. The patch is then peeled from a siliconized or other suitable release coating on the support configuration leaving the drug-imbibed pads now permanently attached to the electrodes of the patch by the peripheral adhesive. Finally, the patch is applied to the patient. Multiple embodiments or variations around this basic concept and method are contemplated.

Embodiments with a separate alignment fixture component or guide element are assembled by registering alignment openings in drug pack and iontophoretic patch support structures consecutively with guide members on an alignment fixture or guide element. The drug pack on its flat substrate is first assembled on the guide element and the lid is removed as in other embodiments. Next, the iontopatch is assembled on top of the open drug pack which again places gel-imbibed pads of the drug pack in alignment with corresponding electrodes. This again results in a combined configuration in which the drug-imbibed pads are permanently bonded to the electrodes by peripheral adhesive and in which the assembly can be separated and applied to a patient. In alternate embodiments, the guide element can be packaged assembled and carrying the blister or drug pack component and the iontophoretic patch component assembled to that combination or the iontophoretic patch component can be packaged assembled to the guide element and thereafter combined with the drug pack component.

BRIEF DESCRIPTION OF THE DRAWINGS

In the drawings wherein like characters denote like parts throughout the same:

FIG. 1A is an exploded cross sectional view through an embodiment of a folding iontophoretic drug delivery system;

FIG. 2 is a top view of the embodiment shown in section in FIGS. 1A and 1B;

FIGS. 3A-3D are cross sectional views illustrating a step-wise activation and deployment of the device of FIG. 4;

FIG. 4 is a top view of the embodiment in FIGS. 3A-3D with the formed lid removed from the drug package;

FIG. 6 is a top view of the embodiment shown section in FIGS. 5A-5E as assembled;

FIGS. 7A and 7B are top and cross sectional views, respectively, of the absorbent pad of the embodiment of FIG. 6;

FIGS. 8A and 8B are top and cross sectional views, respectively, of an alternative embodiment of an absorbent pad;

FIG. 9A is a side view of a folding iontophoretic drug delivery system in accordance with the invention in a folded packaged (stored) configuration;

FIG. 9B is a top view of the packaged configuration of FIG. 9A;

FIG. 10 is a top view of an alternative embodiment of the device in an opened, flat configuration;

FIG. 11A depicts an exploded cross-sectional view through an alternate embodiment of the device of the present invention with separate iontophoretic patch and drug pack components and a guide element;

FIG. 11B is a cross-sectional view depicting the exploded parts of FIG. 11A assembled together;

FIG. 11C depicts the separation for use of the assembled transdermal iontophoretic drug delivery system of FIGS. 11A and 11B;

FIG. 13 is an exploded cross-sectional view of another embodiment alternative to that shown in FIGS. 11A-11C with the drug pack carried by the guide element; and FIG. 14 is an exploded cross-sectional view of still another embodiment alternative to that shown in FIGS. 11A-11C.

DETAILED DESCRIPTION

The invention provides for a fully functional, self contained, easy-to-use iontophoresis device in the form of a pre-packaged drug delivery system which enjoys a relatively long stable shelf life. The system contains a drug reservoir pack, folding panel support structure construction, and a transdermal patch containing a power source, current controlling electronics, and electrodes. The device is ready to use and requires only a few simple operations to activate and apply the patch to a treatment site. The operations in some embodiments consist of removing a drug pack barrier lid, folding the panels onto themselves, and peeling the patch from a release coating. In others, the transdermal patch and drug pack are assembled on an alignment fixture or guide element which is then removed. Several preferred embodiments of the devices will be described below to illustrate the concepts of the invention, but they are not meant to limit the scope of the inventive concept in any manner.

Figure 1B:
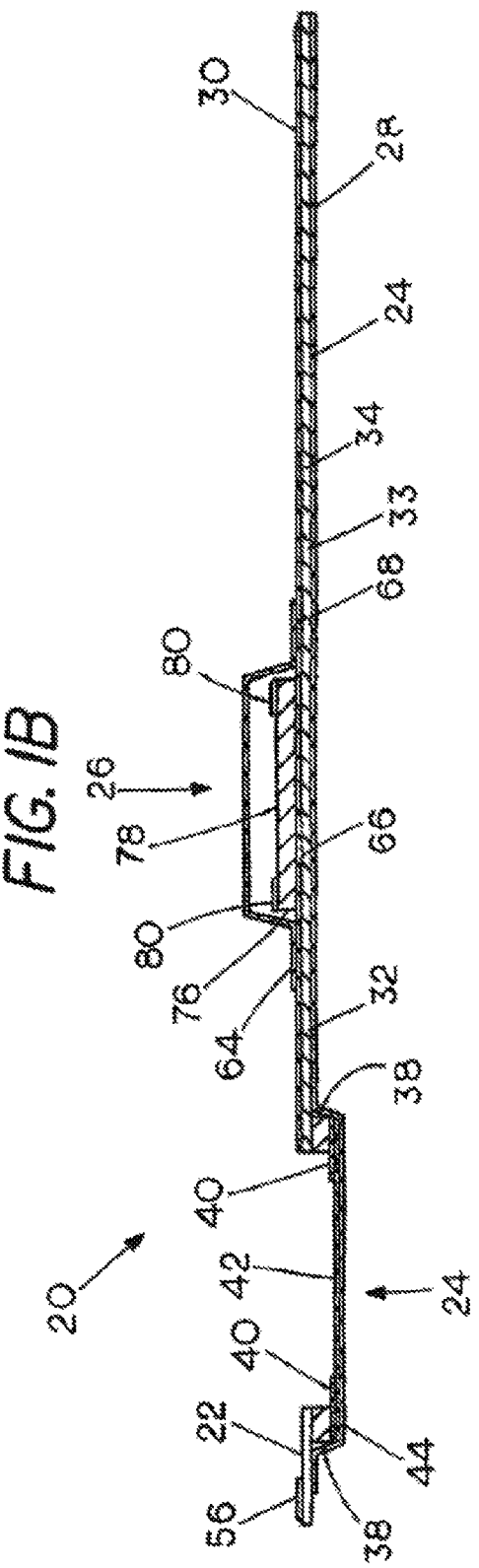
FIG. 1B is an assembled view of the device shown in FIG. 1A.

FIGS. 1A, 1B, and 2 respectively show exploded cross sectional, assembled cross sectional, and top views of one embodiment of a folding device, generally at 20, in an opened or flat configuration. FIGS. 9A and 9B respectively show the embodiment in a side cross sectional and top view of the device folded in a packaged configuration for long term storage. The device consists of 3 main elements: a folding support structure 22, a transdermal iontophoretic patch 24, and a drug containing pack or blister pack 26.

Figure 1C:
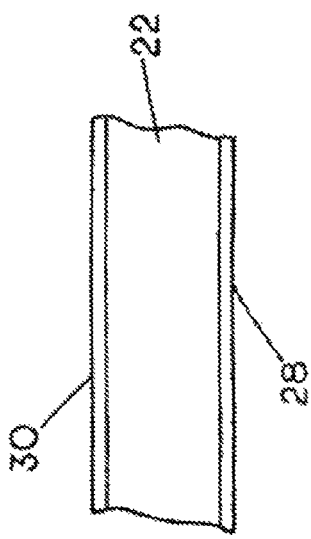
FIG. 1C is a greatly enlarged, fragmentary cross section of a portion of the folding support structure of FIGS. 1A and 1B showing release coating and printable layers.

The folding support structure 22 may include a paperboard, or similar material, substrate with a release coating layer 28 applied to one side and a printable coating 30 applied to the opposite side. FIG. 1C is a greatly enlarged representative fragmentary cross section of a portion of the folding support structure 22, further illustrating the coating layer 28 and printable coating 30. The release coating layer 28 may be a siliconized coating and the printable coating 30 may be a clay coating. An alternative folding substrate or support layer may be a thermoformable polymer or the like. The support structure 22 may contain several fold lines as at 32, 33 and 34 that are created by perforating, scoring, and/or creasing. In the case of a thermoformable substrate, living hinges may be thermoformed at 32, 33 and 34. Depending on the number of fold lines, the support structure may be divided into a number of panels which provide areas to attach various components of the device, apply printing for directions, and/or provide a release coated barrier for exposed adhesives on one panel from permanently sticking to other panels when folded together during storage.

As shown, transdermal iontophoretic patch 24 is adhesively attached to a first panel 36A of the support structure 22 on the release coated side of the substrate. The transdermal iontophoretic patch 24 includes an adhesive coated foam layer 38, an occlusive double sided tape layer 40, an electrode subassembly layer 42 consisting of a power source, electronics and electrodes to operate the patch (not shown), and an overlay tape layer 44. As shown in FIG. 1B, the adhesive side of the foam and the overlay tape are attached to the release coated side of the support structure.

As shown in FIG. 2, cut outs in the foam layer 38 and support structure 22 layers create an empty anode well or recess 46 and an empty cathode well 48 aligned to receive the corresponding anode and cathode imbibed drug pads, preferably gel pads during assembly/activation. The anode and cathode cut outs 46, 48, respectively, expose underlying electrodes, including anode 50 and cathode 52. A half-panel release liner 54 is created by perforating the first panel 36A as also shown in FIG. 2. The half-panel release liner 54 serves to peel the patch off of the substitute layer of the support structure after it is activated.

The half-panel release liner serves the purpose of stiffening the flexible patch to aid in application and additionally allows the operator to handle the patch easily without the patch sticking to the operator's fingers. Preferably, the half of the patch not covered by the half-panel release liner 54 is affixed to the patient's skin first. Subsequently, the half-panel release liner is removed by peeling at a tab 54A of the half-panel release liner. Finally, the other half of the patch is affixed to the patient's skin.

A strip of double-sided tape 56 is attached to the printable side of the support structure 22 on the first panel 36A. The adhesive strip 56 serves a dual function of keeping the structure closed during its long term storage condition by temporarily bonding to a release coated side as shown in FIG. 9A. The second function is to permanently bond to a second panel 36B of the support structure when the parts are folded together to transfer the anode and cathode gel pads 60, 62 as shown in FIG. 3C so that the first panel 36A cannot be re-opened.

As shown in FIG. 9A, the support structure also includes third and fourth panels 36C and 36D, respectively. Third and fourth panels 36C and 36D collectively make up a separator component that is configured to physically separate the drug pack and iontophoresis patch components when the iontophoretic drug delivery system is present in a folded storage stage. The third and fourth panels 36C and 36D of the support structure 22 as folded create a release coated barrier that prevents the occlusive tape 40 in the transdermal patch 24 from touching and permanently sticking to the formed lid layer 64 of the drug pack 26 during long term storage.

As shown in FIG. 2, when the system is present in a pre-folded state prior to storage, the drug pack components are present in the center region of the support structure and flanked on a first side by the iontophoresis patch component and on a second side opposite the first side by the separator component of the support structure which affords both structured separation and external protection for the stored system.

A second piece of double-sided tape 66 is attached to the second panel 36B on the printable side of the support structure 22 to permanently bond the drug containing blister pack 26 to the support structure 22. Alternatively, for example, instead of a double-sided adhesive 66, the drug containing blister pack 26 could be heat sealed to the support structure 22 as by applying a heat seal coating to the bottom of the drug containing pack or to the printable side of the support structure.

As indicated, the drug pack 26 is provided with a formed barrier lid having low moisture vapor permeability, a generally flat bottom layer, containing two spaced gel locations, one containing an anode gel-imbibed non-woven pad 60, another containing a cathode gel-imbibed non-woven pad 62. The low moisture vapor permeable barrier formed lid layer is shown at 64. Preferably, the generally flat bottom layer 68 is constructed of an aluminum foil composite film that may or may not contain a heat seal coating (not shown) on the side that contacts the gel pads. If it is used, the heat seal coating is preferably a readily peelable coating. The gel-imbibed pads as at 58 are constructed of a composite or laminated non-woven material. The anode and cathode gels are dispensed onto the pads and soak into the composite nonwoven material.

The low moisture vapor permeable formed lid layer 64 has been successfully constructed from a cold-formable aluminum composite material consisting of a seal layer on the product contacting under side and a nylon layer on the opposite side. Alternatively, for example, the product contact side 64 may consist of PVC with no seal layer. If a seal layer is employed, preferably it is a peelable heat seal coating. Anode 72 and cathode 74 cavities may be mechanically formed with traditional cold form tooling using Teflon® (polytetrafluorethylene) plugs or in combination with vacuum or pressure assist. The material may be thermoformed if using an alternative material including other fluorinecontaining plastics in sheet or film form such as material sold under the trademark Aclar®, PVDC, and other low moisture vapor transmission barrier thermoformed packaging materials.

FIGS. 7A and 7B show top and side cross-sectional views, respectively, illustrating the structure of one embodiment anode 72 or cathode 74 composite pad materials. As indicated, the anode and cathode pad composite materials are preferably of a non-woven structure to maintain the continuity of the drug-containing material in the structure and may include a plurality of layers, possibly up to three layers, of material. These may include a thick needle-punched polypropylene layer 76, a thin, permeable polyethylene net layer 78, and a thin, occlusive polypropylene layer 80. The layers may be heat fused together without requiring adhesives. All three layers are cut to have the same outside perimeter shape. The occlusive layer 80 is cut to the shape of a perimeter ring that remains intact and occlusive. Inside the ring, the occlusive layer 80 is cut out completely or perforated so that the inside region 84 becomes permeable. The permeable region 84 is shaped to coincide with the shape of the anode 50 and cathode 52 electrodes, by allowing the gel to migrate through this layer and contact the full area of the electrodes when the device is assembled for use. Importantly, the occlusive ring 80 provides a barrier for gel migration so the outside surface remains relatively dry during storage to aid in adhesive transfer of the drug-imbibed pad 70 during activation of the device.

In one embodiment, both the anode 72 and cathode 74 composite pads are similar in shape. Of course, the electrodes may be any convenient shape and the electrodes in a given patch embodiment may be of like or different shapes. FIGS. 8A and 8B show a plan view and cross sectional view of an alternate shape of what may be either an anode and/or cathode of composite nonwoven material 86. This embodiment has a shaped perimeter ring 88, with permeable inside area 90. FIG. 10 is a top view of an alternative embodiment showing a device 100 with a drug pack 102 having anode and cathode formed cavities, 104 and 106, respectively, of different shapes. In similar fashion, anode and cathode formed cavities of different, but corresponding shapes, are reflected in the anode 108 and cathode 110 in the foam, support structure 112, and occlusive layers 114 and 116. Only corresponding components that fit together in an assembled device need be of like shape.

An important aspect of the invention involves shelf life stability of the co-packaged iontophoretic devices. This is of paramount concern based on the history of such devices which have had limited commercial success because of shelf life limitations. As indicated, co-packaging techniques have included attempts to package the wet drug gels in direct contact with the electrodes during long term storage, and attempts to isolate the power source and electronics in the same package through low moisture permeable (high barrier) materials. Wet gels have been packaged in direct contact with the electrodes only and connected to a power source and electronics by a cable or other connector at time of use. As indicated, each of these is fraught with challenges for long term stability. For example, in time, wet gels may degrade the metals in the electrodes, power source, and electronics which, in turn, contaminates and degrades the stability of the gel.

In the present development, stable long term co-packaging is realized by the provision of a storage container for the anode and cathode gels in the form of a separate hermetically sealed drug pack or blister cavity with product contact layers that do not leach into the gel, react with the gel, or absorb the gel. Since the gel material itself provides no form, a carrier substrate material is used to give the gel form and structure, and provide a stable support to facilitate transfer of the gel out of the long term storage container when the system is assembled for use. The carrier substrate should be composed of materials that do not leach, react, or absorb the constituents of the gel. Preferably the blister cavity and carrier substrate should be made from stable, relatively inert, materials such as polypropylene and polyethylene. Any suitable material can be used and may be selected based on the nature of the gel.

Shelf life stability will vary with the construction of the patch component and the stability of the integrity of the drug composition. Patch shelf life depends on retention of adhesive quality and the maintenance of the specified function of the electrical circuit components. The device should have a stable shelf life of at least two (2) years.

FIGS. 5A-5E show in step-wise cross sectional views of one method for forming, filling, and sealing a drug-containing pack or drug pack in accordance with the present development. FIG. 6 shows a top view of the drug pack of FIG. 5, as assembled generally at 120. In the method of FIGS. 5A-5E, the drug containing pack is assembled in an inverted position. The assembly starts with the provision of a lid or cover membrane 122 of a low moisture vapor transmission material formed to create anode and cathode gel cavity shapes 124 and 126, respectively, at a specified spaced interval and depth. Next, an anode pad 128 is placed into the formed anode cavity 124, and likewise, a cathode pad 130 is placed into the formed cathode cavity 126. The pads may be of similar construction to those shown in FIGS. 7A-7B and 8A-8B. The anode and cathode pads are oriented so that each occlusive layer 132, 134 is placed facing into the cavity and in contact with the bottom of the corresponding formed cavity. The anode and cathode pads are sized to just fit in the bottom of the formed cavities. In this manner, the formed cavities then initially provide registration of the pads to the formed lid layer 122.

The remaining steps are performed in a timed sequence as will be described. Allowable open time for the assembly is determined by the rate of pad permeation which is related to the viscosity of the gel used.

Figure 5A:
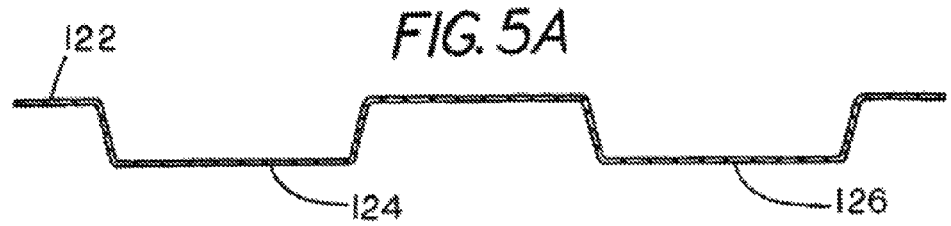
FIGS. 5A-5E are cross sectional views illustrating a step-wise method and design for packaging the drug and saline gels on non-woven absorbent pads.
Figure 5B:
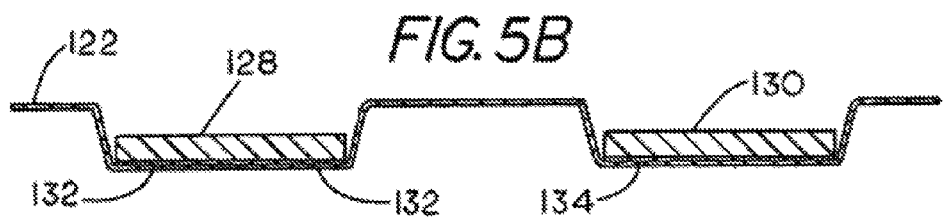
Figure 5C:
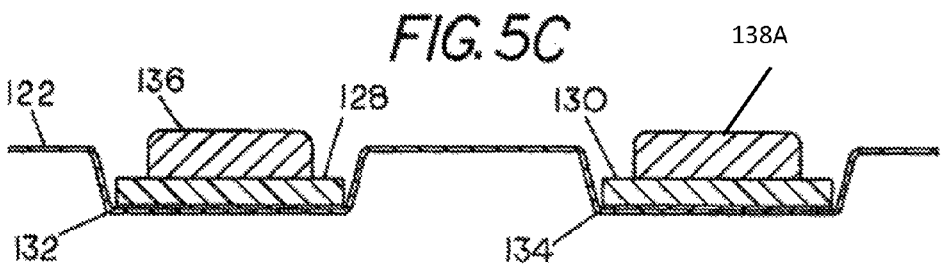
Figure 5D:
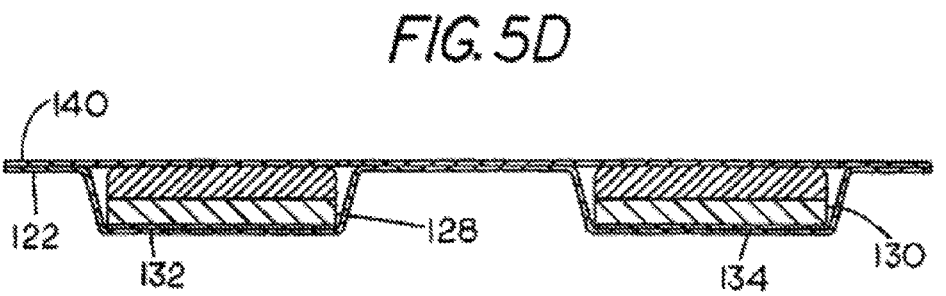

At time $t=t_0$, as shown in FIG. 5C, an amount of a viscous anode gel 136 is dispensed to uniformly cover the central permeable region as at 84 (FIG. 7A) of the anode pad 128; similarly, an amount of a viscous cathode gel 138A is dispensed to uniformly cover a permeable region of the cathode pad 130. As also seen in FIG. 5C, both the anode and cathode gels are dispensed in a manner such that for a given amount of gel, once dispensed, the total height of the pad plus the gel height somewhat exceeds the depth of the formed anode or cathode cavity 124 or 126. The gel must be of a relatively high viscosity range in order for it to maintain its shape/height for a necessary duration during assembly of the device. At time $t>t_0<t_1$, a flat bottom or carrier substrate layer 140 is applied (FIG. 5D) and heat sealed to the formed cover membrane 122. Application of the flat carrier substrate layer 140 contacts and compresses the gel causing the gel to wet the inner surface of the carrier substrate layer 140 and spread out as also shown in FIG. 5D.

Alternatively, in another embodiment (not shown), the flat bottom layer can be formed similarly to the formed cover membrane layer to create a nested configuration, in which case, the gel plus the pad height can be designed so that when the bottom and lid layers are assembled, the gel will be in contact with the carrier substrate layer in a similar manner as in the illustrated embodiment.

In this procedure, time span $t=t_0$ to $t=t_1$ is defined as the time it takes the dispensed anode and cathode gels to soak through their respective pads and start to wet to the bottom of the formed cavities of 11d layer. Time is a factor because it has been found that if the gels soak completely through the respective pads and wet the bottom or inner surface of the formed cover membrane cavity before the carrier substrate layer is applied, the pads, once fully imbibed, may preferentially stick to the inside of the formed lid. This, of course, is undesirable as the imbibed gel pad would adhere to the lid layer 122 instead of the carrier substrate layer 140 when one attempted to assemble the system. Time span $t=t_0$ to $t=t_1$ also defines the time in which the gel will adequately maintain its height so that the gel will wet and adhere to the inner surface of the bottom layer 140 when that layer is applied.

For the above reasons, the gels are formulated in a preferred viscosity range to provide the correct flow rate and surface tension. For example, a 100,000 centipoise gel may have a $t_0$-$t_1$ time window of about 2-4 minutes. This is adequate for normal assembly to occur.

Figure 5E:
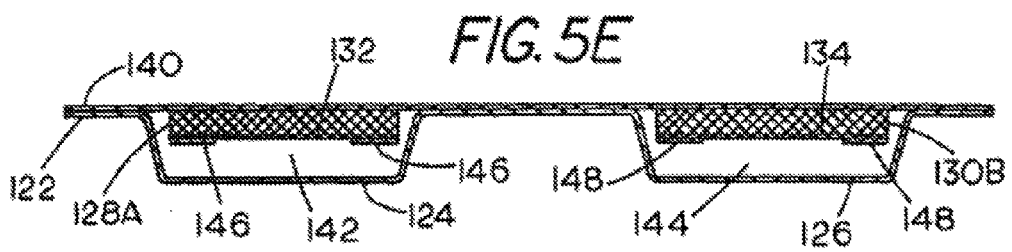

In this process, the gels initially contact and wet the bottom layer member 140. This allows the gels to act as adhesives as the surface tension of the gels between the member 140 and the pads 128 and 130 exceeds the gravitational forces on the imbibing pads. Therefore, as the pads slowly imbibe with gel, they will stick to and be pulled towards the carrier substrate layer regardless of the orientation of the device. Thus, after the bottom and lid layers are sealed, the compressed gels imbibe (soak-in) into the anode and cathode pads respectfully, creating a fully imbibed non-woven anode pad 128A and fully imbibed pad 130B as shown in FIG. 5E. As described previously, the fully imbibed anode and cathode gel pads continue to adhere to the bottom layer 140 thereby creating anode and cathode headspaces 142 and 144, respectively in the package as also shown in FIG. 5E. It has been found that due to the high surface tension and high preferred viscosity of the gels, the fully imbibed pads will remain registered to their respective formed lid cavities and be attached to the carrier substrate layer as shown throughout the anticipated shelf life of the device.

It will be appreciated that the amount of gel added to each cavity should be matched to the absorbency of each pad in order to minimize excess gel. The amount and viscosity of the gels is preferably such that imbibed gel does not wet the outer surface of the occlusive ring on the pads. In this manner, the outer surface of the occlusive ring 146, 148 should remain relatively dry to aid adhesive transfer and adhesive attachment of imbibed gel pads into corresponding empty anode and cathode wells of the transdermal patch during activation. The inside surface of the formed lid cavities in the anode and cathode headspace regions as at 142 and 144 should remain free of gel and relatively dry.

In order for this packaging concept to function, the gels must be formulated with a preferred viscosity. The preferred range is between 8,000-120,000 centipoise but is not limited so long as the process can be successfully followed. The gels useful in the system may be formulated by dissolving an appropriate amount of drug or saline in water, and adding a gelling agent such as HPMC (hydroxypropylmethylcellulose) such that a conductive gel of appropriate viscosity is created. Other gelling agents, such as PVP (polyvinylpyrrolidone), PEO (polyethyleneoxide), or PVA (polyvinylalcohol) can also be used. Successful gels have been formulated from a HPMC powder at 2% w/w.

The concentration of an active agent in the gel may vary widely depending on the agent of interest and the desired patch dosage and planned duration of application. Generally, the concentration will range from about 0.2% to 10% (weight).

FIGS. 3A-3D show in step-wise fashion, in cross-sectional views, how one preferred embodiment is activated and deployed to a treatment site. FIG. 4 shows the top view of FIG. 3A after the blister or drug pack lid 64 has been removed. FIGS. 9A and 9B show a side sectional and top view, respectfully, of a fully packaged device.

Beginning with the fully packaged device of FIGS. 9A and 9B, a deployment or assembly process will be described. First, the fully packaged device is opened and unfolded by pulling at the tab 160 to release adhesive strip 56 from the release liner coated side of panel 36D. Second, the formed cover membrane layer 64 is removed or peeled away from the bottom layer 68 exposing the gel-imbibed anode and cathode pads 60, 62 which are adhered through surface tension of the gels to the bottom layer 68 as shown in FIG. 3A. The peel is initiated by peeling at the tab 78 (FIG. 2) on the formed lid member 64.

Next, the first panel 36A is folded at the fold line 32 onto the second panel 36B, thereby bringing the occlusive region as at 80 of the occlusive layer 80 of the anode and cathode gel pads 60, 62 in permanent adhesive contact with the occlusive tape layer 40 of the transdermal patch 24 as shown in FIG. 3C. Also, the adhesive strip is brought into contact with the printable coating layer 30 of the support structure 22 and is permanently adhered to the second panel 36B, thereby preventing the panel 36A from being re-opened. FIG. 3B shows an intermediate view of the folding action. The outer surface of the transdermal patch is preferably pressed to ensure good permanent bonding of the occlusive tape 40 to the occlusive region as at 80 on the gel pads.

Finally, the half release liner 54 is peeled from the support structure at the tab 54A bringing the fully assembled transdermal patch 170 with it. The exposed half of the patch adhesive can be applied to the treatment site and the half release liner 54 thereafter can be peeled from the transdermal patch at the tab 54B (FIG. 9B) and the remaining half of the patch adhered to the treatment site.

Figure 12:
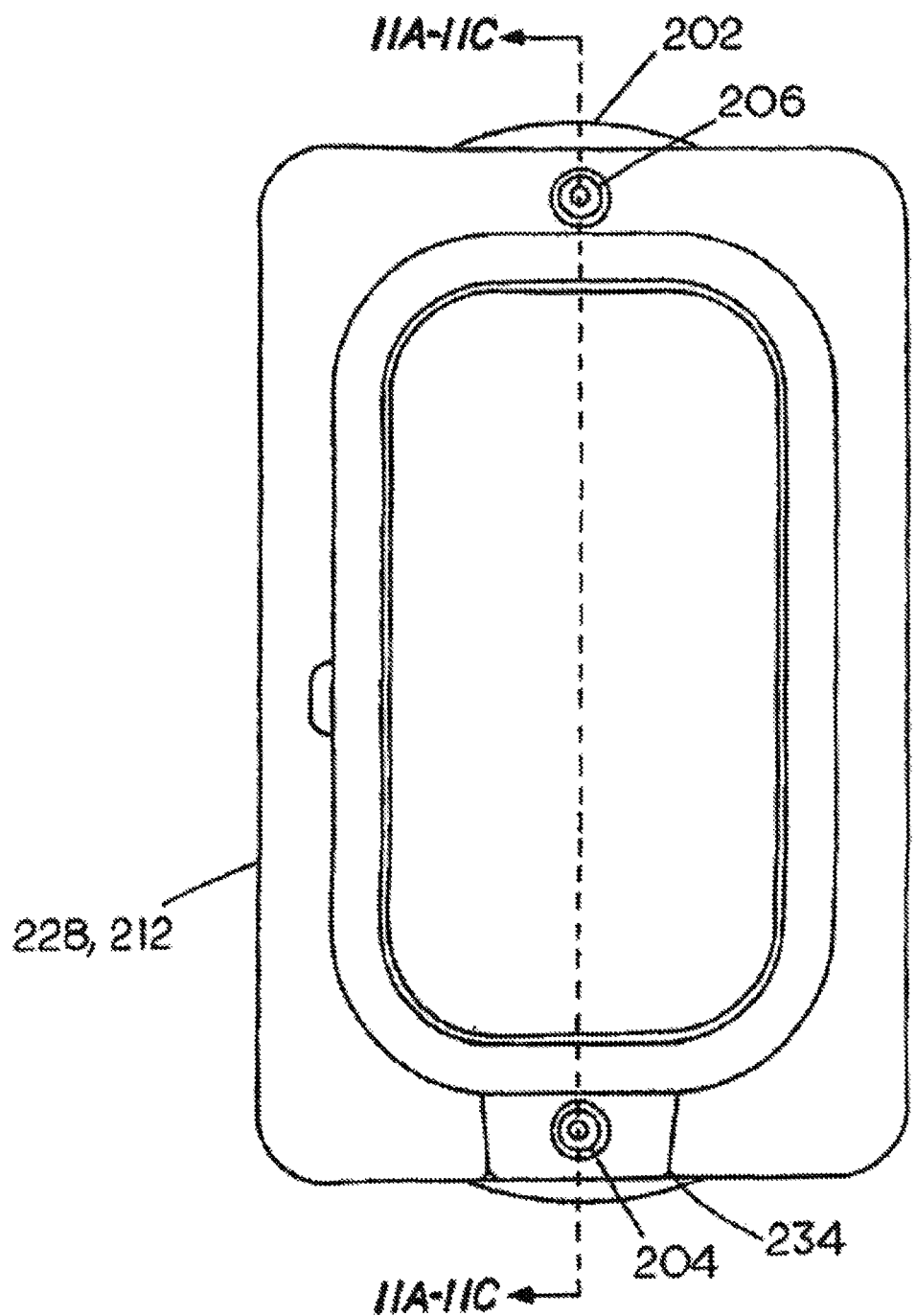
FIG. 12 is a top view of the assembly of FIG. 11B.

FIGS. 11A-11C illustrate an alternative embodiment including an alignment fixture or guide element and illustrating activation of the embodiment. FIG. 12 shows a top view of the fully assimilated embodiment of FIG. 11B from which the cross-sectional views of 11A-11C are taken. As best seen in FIG. 11A, the device, generally 200, as packaged, includes three main components. They are a guide element 202 having spaced raised alignment members 204, 206, a drug pack arrangement 208 and a transdermal patch assembly 210. The main components are designed to be stored separately in a common package and assembled when the device is prepared for use.

The drug pack includes a flat card substrate layer 212 which is designed with spaced alignment openings 214 and 216 which register with alignment members 204 and 206 during assembly. Anode and cathode non-woven, gel-imbibed pads 218 and 220 are respectively carried on a bottom layer 222 and separated from drug pack lid 224 in the manner of embodiments previously described and illustrated in FIGS. 5A-5E. Drug pack 208 is adhered to card substrate layer 212 as by a double-sided tape layer at 226.

The transdermal patch component 210 is mounted on a flat card substrate layer 228 with spaced alignment openings 230 and 232 and, as with previously described embodiments, half release liner 234. The patch assembly may be quite similar in construction to that previously described with foam layer 236 and double-sided tape 238, electrode subassembly layer 240 and overlaying tape layer 242.

At the time of use, individual components are aligned and assembled to each other using features of a component to self-align to adjacent components. In this manner, the guide element 202 may be positioned on a flat surface with the spaced alignment members 204, 206 facing up as shown in FIG. 11A. Next, the drug blister pack 208 is assembled to the alignment fixture or guide element 202 by registering alignment member 204 to the opening 214 in the drug pack and alignment member 206 to opening 216. The lid 224 can then be peeled off the drug pack 208 exposing the gel-imbibed, non-woven anode and cathode pads 218 and 220, respectively. Next, the transdermal iontophoresis patch 210 can be assembled to drug pack 208 by again using alignment members 204 and 206 with alignment openings 230 and 232 thereby placing the gel-imbibed pads in alignment with corresponding electrodes. This results in the combined configuration depicted in the cross-sectional view of FIG. 11B and top view of FIG. 12 with the drug pack arrangement 208 and the transdermal patch assembly 210 in consecutive assembled registration on the guide element 202.

In this stacked condition, the assembled patch is ready to be separated for placement on a patient. Separation can be accomplished by simply peeling the half release liner 234 from the card thereby separating the device from the card substrate layer 228 and bringing the fully assembled transdermal patch 250 with it as shown in FIG. 11C. The patch is then ready to be applied to the patient as described in relation to the previous embodiments.

It will be appreciated that the drug pack 208 and the transdermal patch 210 are similar in construction to previously described embodiments except that the card substrate layers in this embodiment are separate flat members rather than folding connected panels. The flat card substrate layers 212, 228 include alignment openings corresponding to the members 204 and 206 on guide element 202 and they do not require a silicon or other release coating so that both sides may contain a printable clay coating material or the like.

The card layers 212, 228 may also be constructed from any suitable polymer material. The alignment members 204 and 206 of the guide element 202 are preferably thermoformed or injection molded out of a suitable polymer material also.

FIG. 13 is an exploded cross-sectional view of an alternate embodiment to that shown in FIGS. 11A-11C in which a guide element 302 with alignment members 304 and 306 is substituted in the drug pack 308 for the flat card substrate layer 212. The drug pack is otherwise similar to previously described drug packs and a lid is shown at 324. The transdermal patch component 310 is also similar to that shown in FIG. 11A and includes substrate 328 with spaced alignment openings 330 and 332 and half release layer at 334. The drug pack 308 is bonded to the guide element 302 by double-sided tape 326.

Assembly and activation is similar to that of the embodiment of FIG. 11A-11C. Thus, the drug pack lid 324 is removed and the transdermal patch 310 is aligned with the drug pack over the alignment members 304 and 306 using the openings 330 and 332. The assembled patch thereafter being peeled away in the manner of FIG. 11C.

FIG. 14 shows an exploded cross-sectional view of yet another embodiment of the device of the present invention which represents another alternative to that shown in FIGS. 11A-11C. In this embodiment, the alignment fixture 402 with alignment members 404 and 406 is substituted for the release card substrate layer 228 associated with the transdermal patch component 410. The alignment fixture includes a silicone release coating on upper surface 402A applied to the side to which the patch adheres prior to removal. This embodiment is assembled and applied in a similar manner to those described just above. Thus, the lid 424 of the drug pack 408 is removed and the openings 414 and 416 in the substrate 412 are aligned with the members 404 and 406 and the fully aligned device is peeled away in the manner of FIG. 11C.

It will further be appreciated that the assembled device or patch to be applied to a user may be of any convenient size as from as small as about 1 cm×2 cm to about 15 cm×20 cm. The size can vary widely depending on the active agent administered and the condition to be treated.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. An iontophoretic drug delivery system for pre-use assembly comprising:
    (a) a drug pack component comprising one or more gel pads;
    (b) an iontophoresis patch component;
    (c) wherein said iontophoresis patch component is configured to align said gel pads of said drug pack component in conductive relation in an assembled state; and
    (d) an alignment structure to assist in assembling said components, wherein said alignment structure is selected from;
    (1) a folding support structure associated with said drug pack component and said iontophoresis patch component, said folding support structure comprising a separator component configured to be interposed between and thereby physically separate and protect said drug pack and iontophoresis patch components when said iontophoretic drug delivery system is present in a fully folded storage stage,
    wherein said folding support structure comprises a first panel having thereon said iontophoresis patch component, and a second panel having thereon said drug pack component comprising said gel gads and joined to said first panel on a first side of said second panel, and wherein said separator component comprises a third panel joined to said second panel on a second side of said second panel that is opposite said first side; and
    (2) a guide element for separate consecutive alignment of said drug pack component with said iontophoresis patch component;
    wherein said drug pack component comprises a drug pack support structure separate from the alignment structure, said iontophoresis patch component comprises an iontophoresis patch support structure separate from the alignment structure, and said alignment structure comprising said guide element comprises a flat substrate comprising spaced raised alignment members for aligning the drug pack component with the iontophoresis patch component;
    wherein said alignment structure comprises a multi-panel folding support structure associating said drug pack component said iontophoresis patch component and said separator component.

2. The iontophoretic drug delivery system as in claim 1 wherein said drug pack component and said iontophoresis patch component are provided on separate conjoined panels of said folding support structure.

3. The iontophoretic drug delivery system as in claim 2 wherein said support structures are connected.

4. The iontophoretic drug delivery system as in claim 1 wherein said folding support structure assumes one folded configuration for storage and a different folded configuration for assembly of said system.

5. The iontophoretic drug delivery system as in claim 1 wherein said support structure comprises four conjoined folding panels.

6. The iontophoretic drug delivery system as in claim 1 wherein said drug pack component and said iontophoresis patch component are provided on separate support structures and wherein said alignment structure comprises said guide element associated with at least one of said separate support structures.

7. The iontophoretic drug delivery system as in claim 6 wherein said guide element includes raised alignment members and said separate support structures include corresponding openings to receive said alignment members therethrough.

8. The iontophoretic drug delivery system as in claim 6 wherein one of said separate support structures is attached to said guide element prior to assembly of said system.

9. The iontophoretic drug delivery system as in claim 1 wherein said drug pack component comprises said gel pads including an anode gel pad and a cathode gel pad isolated prior to assembly by a cover membrane having low moisture permeability.

10. The iontophoretic drug delivery system as in claim 9 wherein said gel pads comprise one or more layers of non-woven polymer matrix.

11. The iontophoretic drug delivery system as in claim 9 including an amount of therapeutic agent ion species located in gel associated with at least one of said gel pads.

12. The iontophoretic drug delivery system as in claim 11 wherein said therapeutic agent is present in said gel in a concentration from about 0.2% to 10%.

13. The iontophoretic drug delivery system as in claim 9 wherein said gel pads are fixed to a substrate layer in said drug pack by adherence of a gel material prior to assembly of said system.

14. The iontophoretic drug delivery system as in claim 9 wherein said cover membrane having low moisture permeability comprises a material selected from the group consisting of metal/polymer composites and PVC.

15. The iontophoretic drug delivery system as in claim 1 including an amount of therapeutic species in said iontophoresis patch.

16. The iontophoretic drug delivery system as in claim 1 wherein said iontophoresis patch component includes electrodes comprising an anode and a cathode and a source of electric power.

17. The iontophoretic drug delivery system as in claim 16 wherein said drug pack component comprises said gel pads and said electrodes are contained in recesses adapted to receive said gel pads of said drug pack upon assembly of said system into said assembled state.

18. The iontophoretic drug delivery system as in claim 1 further comprising a peripheral adhesive layer bonding said gel pads to said electrodes in said assembled state.

19. The iontophoretic drug delivery system as in claim 1 wherein the folding support structure comprises three fold lines.

20. The iontophoretic drug delivery system as in claim 19, wherein each of the three fold lines extends from a first end to a second end of the folding support structure.

21. The iontophoretic drug delivery system as in claim 1 wherein the separator component comprises a fourth panel of the support structure adjacent to the third panel and connected to the third panel by a fold line, and wherein the first panel is connected to the second panel by a fold line, the second panel is connected to the third panel by a fold line.

22. The iontophoretic drug delivery system as in claim 1 wherein the drug pack component comprises a pair of said gel pads on the second panel and wherein the iontophoresis patch component comprises first and second electrodes on the first panel and is configured to align the first and second electrodes respectively with the pair of said gel pads in conductive relation in an assembled state.

23. The iontophoretic drug delivery system as in claim 1, wherein being associated with comprises being heat-sealed or adhesively attached.

24. The iontophoretic drug delivery system as in claim 23, wherein the folding support structure comprises a front surface and a back surface, and wherein the iontophoresis patch component is associated with the back surface of the folding support structure and the drug pack component is associated with front surface of the folding support structure.

25. An iontophoretic drug delivery system for pre-use assembly comprising:
   (a) a drug pack component comprising one or more gel pads;
   (b) an iontophoresis patch component;
   (c) wherein said iontophoresis patch component is configured to align with one or more gel pads of said drug pack component in conductive relation in an assembled state; and
   (d) an alignment structure to assist in assembling said components, wherein said alignment structure is selected from;
   (1) a folding support structure associated with said drug pack component and said iontophoresis patch component, said folding support structure comprising a separator component configured to be interposed between and thereby physically separate and protect said drug pack and iontophoresis patch components when said iontophoretic drug delivery system is present in a fully folded storage stage, wherein said folding support structure comprises a first panel having thereon said iontophoresis patch component, and a second panel having thereon said drug pack component and joined to said first panel on a first side of said second panel, and wherein said separator component comprises a third panel joined to said second panel on a second side of said second panel that is opposite said first side; and
   (2) a guide element for separate consecutive alignment of said drug pack component with said iontophoresis patch component;
wherein said drug pack component comprises a drug pack support structure separate from the alignment structure, said iontophoresis patch component comprises an iontophoresis patch support structure separate from the alignment structure, and said alignment structure comprising said guide element comprises a flat substrate comprising spaced raised alignment members for aligning the drug pack component with the iontophoresis patch component and wherein the drug pack support structure comprises openings to receive the alignment members therethrough during alignment and the iontophoresis patch support structure comprises openings to receive the alignment members therethrough during alignment.

* * * * *